United States Patent [19]

Kraft et al.

[11] 3,943,085
[45] *Mar. 9, 1976

[54] SUSPENSION COPOLYMER COMPOSITION

[75] Inventors: Paul Kraft, Spring Valley; Siegfried Altscher, Monsey, both of N.Y.

[73] Assignee: Stauffer Chemical Company, Westport, Conn.

[ * ] Notice: The portion of the term of this patent subsequent to Jan. 27, 1993, has been disclaimed.

[22] Filed: Feb. 7, 1975

[21] Appl. No.: 548,060

Related U.S. Application Data

[60] Continuation of Ser. No. 346,198, March 29, 1973, abandoned, which is a division of Ser. No. 49,209, June 23, 1970, Pat. No. 3,725,509.

[52] U.S. Cl. .................. 260/29.6 H; 260/29.6 TA; 260/29.6 MP; 260/80.71; 260/DIG. 24
[51] Int. Cl.$^2$ .......................................... C08F 230/02
[58] Field of Search 260/29.6 MP, 29.6 H, 29.6 TA, 260/80.71

[56] References Cited
UNITED STATES PATENTS

| | | | |
|---|---|---|---|
| 3,489,706 | 1/1970 | Mikofalvy | 260/29.6 T |
| 3,682,871 | 8/1972 | Mikofalvy et al. | 260/29.6 TA X |
| 3,691,127 | 9/1972 | Kraft et al. | 260/29.6 T |

*Primary Examiner*—Lucille M. Phynes
*Attorney, Agent, or Firm*—Richard P. Fennelly

[57] ABSTRACT

Self-extinguishing, thermoplastic polymer compositions are prepared by the intimate admixture of a thermoplastic polymer with a copolymer of a halogen containing ethylenically unsaturated monomer and a phosphorus containing vinyl monomer, particularly a bis(hydrocarbyl)vinylphosphonate. The thus modified thermoplastic polymers display a high degree of flame retardance without any substantial changes in their physical properties including, for example, their clarity and hardness and the resulting compositions may be safely employed in any application requiring their possible exposure to fire or high temperatures.

11 Claims, No Drawings

SUSPENSION COPOLYMER COMPOSITION

CROSS-REFERENCE TO RELATED APPLICATIONS

This application is a continuation of the now abandoned application Ser. No. 346,198 (filed Mar. 29, 1973) which in turn is a divisional of Ser. No. 49,209 (filed June 23, 1970) now U.S. Pat. No. 3,725,509, granted Apr. 3, 1973.

BACKGROUND OF THE INVENTION

Many thermoplastic polymers such, for example, as the homo- and copolymers of methyl methacrylate, polyolefins, polystyrene and acrylonitrile-butadiene-styrene resins are hard and, in many instances, optically clear materials which are widely utilized for the preparation of a broad range of consumer and industrial articles. As normally prepared, these thermoplastic polymers will ignite and continue to burn upon exposure to flames or high temperatures. However, in many instances, particularly where they are being considered for use in building interiors or in applications requiring their prolonged exposure to high temperatures, it is highly desirable that such polymers should display fire or flame retardant properties so that they may either meet the standards set by various building codes or so that they may be safely employed in place of more costly materials.

Prior attempts to provide fire retardant, thermoplastic polymer compositions have involved the use of a variety of extraneous additives such, for example, as antimony oxides, halogenated paraffins, halogenated hydrocarbons and low molecular weight phosphate esters. However, the effective utilization of these and other additives has ordinarily required their presence in rather high concentrations which adversely affected the physical properties of the treated polymers. Thus, the inherent hardness and, in some instances, the clarity of the thermoplastic polymers were particularly prone to deterioration in the presence of the high concentrations of these additives which were necessary in order to achieve a self-extinguishing polymer composition.

It is, therefore, the prime object of this invention to provide fire retardant thermoplastic polymer compositions by the use of additives whose presence will not adversely affect the inherent physical properties such as hardness and, in some instances, the clarity of the thus modified polymers. It is a further object of this invention to provide a novel class of copolymers which are particularly useful, as additives, for preparing fire retardant, thermoplastic polymer compositions. Various other objects and advantages of this invention will be apparent from the disclosure thereof which follows hereinafter.

TECHNICAL DISCLOSURE OF THE INVENTION

In its broadest aspect, this invention resides in the discovery that thermoplastic polymers may be rendered fire retardant by the incorporation, thereon, of additives comprising copolymers of: (1) one or more halogen containing vinyl monomers with (2) one or more phosphorus containing vinyl monomers as hereinafter defined. More particularly, it has now been discovered that the use of copolymers of one or more halogen containing vinyl monomers with one or more bis(hydrocarbyl) vinylphosphonates provides the thus modified polymers with a high degree of fire retardance without resulting in any serious deleterious effects upon any of their significant physical properties, and particularly their clarity and hardness. Moreover, it is truly surprising and advantageous to find that the polymer blends resulting from the process of this invention display an outstanding degree of compatibility since, as is well known to those skilled in the art, physical blends of two or more polymers are almost always characterized by their inherently poor compatibility.

The novel copolymers suitable for use as fire retardant additives for thermoplastic polymers in the process of this invention comprise copolymers of:

1. One or more halogen containing, alpha, beta-ethylenically unsaturated, i.e. vinyl, monomers including vinyl halides such, for example as vinyl chloride, vinyl fluoride and vinyl bromide; halogenated $C_1$–$C_{12}$ alkyl acrylates and methacrylates such, for example, as methyl alpha-chloroacrylate and methyl alpha-bromoacrylate; vinylidene halides such, for example, as vinylidene chloride, vinylidene bromide, vinylidene chlorobromide and vinylidene fluoride; halo- substituted nitriles of ethylenically unsaturated carboxylic acids such, for example, as alpha-chloroacrylonitrile; and the chlorinated styrenes such, for example, as alpha-chlorostyrene, o-chlorostyrene, m-chlorostyrene, p-chlorostyrene and 2,4-dichlorostyrene; and 2. one or more bis(hydrocarbyl) vinylphosphonates having the structure:

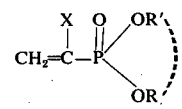

wherein X is selected from the group consisting of hydrogen, halogen, cyano, aryl such as phenyl, $C_1$–$C_{18}$ alkyl and

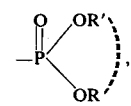

wherein R and R' are hydrocarbyl and substituted hydrocarbyl groups consisting essentially of hydrogen and carbon and containing up to about 18 carbon atoms inclusive with the proviso that R and R' may be the same, different or conjoint, i.e. R and R' may form one single radical.

The use, in this disclosure, of the expression "hydrocarbyl" and "substituted hydrocarbyl groups" refers to the radicals obtained upon the removal of a hydrogen from a hydrocarbon or substituted hydrocarbon group which may be either an aliphatic or aromatic group. These hydrocarbyl groups may be substituted with any non-interfering groups, i.e. with any group which does not interfere with the polymerization of the bis(hydrocarbyl) vinylphosphonate. Such substituent groups include, for example, chloro, bromo, fluoro, nitro, hydroxy, sulfone, ethoxy, methoxy, nitrile, ether, ester and keto groups and the like.

Illustrative of such aliphatic groups as are represented by R and R' are alkyl groups, such as methyl, ethyl, propyl, butyl, pentyl, hexyl, nonyl, pentenyl and hexenyl groups and all of their respective isomers; cycloalkyl groups, such as cyclopropyl, cyclobutyl, cyclopentyl, cyclohexyl and cyclohexenyl groups and the like; while typical aryl groups represented by R and R' include phenyl, benzyl, phenethyl, tolyl and naphthyl groups and the like.

Representative of the above depicted bis(hydrocarbyl) vinylphosphonates are:

Bis(beta-chloroethyl) vinylphosphonate;
Bis(beta-chloropropyl) vinylphosphonate;
Bis(beta-chloroethyl) 1-methylvinylphosphonate;
Bis(beta-chloroethyl) 1-cyanovinylphosphonate;
Bis(beta-chloroethyl) 1-chlorovinylphosphonate;
Bis(beta-chloroethyl) 1-phenylvinylphosphonate;
Dimethyl vinylphosphonate;
Diethyl vinylphosphonate;
Bis(omega-chlorobutyl) vinylphosphonate;
Di-n-butyl vinylphosphonate;
Di-isobutyl vinylphosphonate;
Bis(2-chloroisopropyl) 1-methylvinylphosponate;
Diphenyl vinylphosphonate; and
Bis(2,3-dibromopropyl) vinylphosphonate.

From the above group of bis(hydrocarbyl) vinylphosphonate monomers, it is preferred to employ bis(beta-chloroethyl) vinylphosphonate in preparing the novel copolymers of this invention since the latter monomer is a commercially available material and lower in cost than any of the other bis(hydrocarbyl) vinylphosphonates. It is to be noted, at this point, that the use of the term "copolymer" in this disclosure is meant to apply to polymers derived from two, three or more distinct monomer species.

In addition to the above described bis(hydrocarbyl) vinylphosphonates, it is also possible to prepare copolymers useful as flame retardant additives for thermoplastic polymers by employing: (1) mono(alkyl) acid vinylphosphonates such, for example, as mono(ethyl) hydrogen vinylphosphonate, mono(butyl) hydrogen vinylphosphonate, mono(octyl) hydrogen vinylphosphonate; mono(beta-chloroethyl) hydrogen vinylphosphonate, mono(omega-chlorooctyl) hydrogen vinylphosphonate; (2) mono(cycloalkyl) and mono(aryl) hydrogen vinylphosphonates such, for example, as mono(cyclohexyl) hydrogen vinylphosphonate, mono(phenyl) hydrogen vinylphosphonate, mono(benzyl) hydrogen vinylphosphonate; (3) bis(cycloalkyl) and bis(aryl) vinylphosphonate such, for example, as bis(cyclohexyl) vinylphosphonate and bis(benzyl) vinylphosphonates; and, (4) bis(alkyl), bis(cycloalkyl), and bis(aryl) allylphosphonates such, for example, as bis(beta-chloroethyl) allylphosphonates, bis(cyclohexyl) allylphosphonate and bis(benzyl) allylphosphonate as well as mixtures of any two or more of the above described phosphonate monomers.

The copolymers of this invention may also, if desired, contain one or more optional comonomers including alpha-olefins such as ethylene, propylene and butylene; vinyl esters of carboxylic acids such as vinyl acetate, vinyl butyrate, and vinyl stearate; the $C_1$–$C_{20}$ alkyl esters of acrylic and methacrylic acid such as methyl methacrylate, methyl acrylate, ethyl acrylate, butyl acrylate, 2-ethylhexyl acrylate and lauryl acrylate; aryl, halo- and nitro- substituted benzyl esters of acrylic and methacrylic acid such as benzyl acrylate and 2-chlorobenzyl acrylate; ethylenically unsaturated monocarboxylic-acids such as acrylic and methacrylic acids; ethylenically unsaturated dicarboxylic acids, their anhydrides and their $C_1$–$C_{20}$ mono- and dialkyl esters such as aconitic acid, fumaric acid, maleic acid, itaconic acid, citraconic acid, maleic anhydride, dibutyl fumarate and monoethyl maleate; amides of ethylenically unsaturated carboxylic acids such as acrylamide and methacrylamide; vinyl aryl compounds such as styrene and alpha-methyl styrene; nitriles of ethylenically unsaturated carboxylic acids such as acrylonitrile and methacrylonitrile; $C_1$–$C_{20}$ alkyl vinyl ethers such as methyl vinyl ether, ethyl vinyl ether and stearyl vinyl ether; dienes such as isoprene and butadiene; and, glycidyl esters of acrylic and methacrylic acid such as glycidyl acrylate and glycidyl methacrylate, etc. Preferred for use as optional comonomers are methyl methacrylate, acrylonitrile and methacrylonitrile.

The above described copolymers may be prepared by means of any convenient polymerization technique known to those skilled in the art such, for example, as by means of a free radical, ionically or Ziegler catalyst initiated bulk, emulsion, solution or suspension type polymerization technique.

However, for use as flame retardant additives for thermoplastic polymers, it is preferred that they be prepared by means of a free radical initiated, suspension polymerization process in an aqueous medium containing from about 0.01 to 5%, as based on the total weight of the monomer mixture, of a suspension agent such, for example, as gelatin, starch, hydroxymethyl cellulose, hydroxyethyl cellulose, hydroxypropyl cellulose, carboxymethyl cellulose, talc, clay, polyvinyl alcohol and the like. As a catalyst for the polymerization, one may use from about 0.01 to 5.0%, as based on the total weight of the monomer mixture, of a monomer soluble azo or peroxide compound such, for example, as azobisisobutyronitrile, lauroyl peroxide, benzoyl peroxide, isopropylperoxy dicarbonate, t-butyl peroxypivalate and the like. Polymerization may ordinarily be initiated by heating the system to a temperature in the range of from about −10° to 100°C. for a period of from about 1 to 30 hours with agitation being applied throughout the course of the reaction. The resulting product will comprise an aqueous suspension of the desired copolymers which will be in the form of particulate solids having a resin solids content in the range of from about 5 to 60%, by weight. These copolymer particles will have a particle size in the range of from about 2 to 500 microns with a range of from about 50 to 250 microns being preferred when the copolymers are to be used as additives for preparing flame retardant, thermoplastic polymers. These copolymers should have a molecular weight, as expressed in terms of their Relative Viscosity, of from about 0.5 to 3.0 when determined, at 25°C. with a 1%, by weight, solution of the copolymer in cyclohexanone.

With respect to proportions, these novel copolymers may contain from about 2.5 to 99%, by weight, of one or more of the above described bis(hydrocarbyl) vinylphosphonates with the balance of the copolymer comprising one or more of the above described halogen containing, ethylenically unsaturated monomers together with from 0 to about 50%, by weight of one or more of the above described optional comonomers. Optimum results, as flame retardant additives for thermoplastic polymers, are obtained by the use of copolymers containing from about 2.5 to 60% of one or more bis(hydrocarbyl) vinylphosphonates, preferably bis(beta-chloroethyl) vinylphosphonate.

It is to be noted, with respect to the above described proportions for the composition of the copolymers of this invention, that it has been found that it becomes increasingly more difficult to attain good polymerization conversion rates as attempts are made to increase the amount of the bis(hydrocarbyl) vinylphosphonate in the resulting copolymer substantially above a concentration of about 60%, by weight. On the other hand, the use of these copolymers as flame retardant additives for thermoplastic polymers becomes progressively more inefficient when they contain substantially less than about 5%, by weight, of one or more bis(hydrocarbyl) vinylphosphonates since the resulting blend will then require the presence of a rather high concentration of the copolymer in order to attain flame retardancy. The use of such high concentrations of these copolymer additives may, in turn, result in some deterioration in the inherent physical properties of the thus modified thermoplastic polymer.

Specific copolymer compositions which have been found to provide particularly good results as additives for the preparation of fire retardant, thermoplastic polymer composition are:

1. a copolymer of vinyl chloride with about 10 to 40%, by weight, of bis(beta-chloroethyl) vinylphosphonate, and 2. a terpolymer containing about 10 to 60%, by weight, of vinyl chloride, about 10 to 60%, by weight of vinyl bromide; and about 10 to 60%, by weight of bis(-beta-chloroethyl) vinylphosphonate.

In all cases, the novel copolymers of this invention have been found to provide blends with thermoplastic polymers which are characterized by their outstanding fire retardancy, their excellent compatibility and their retention of physical properties such as hardness, tensile and impact strengths and clarity in those cases where the initial polymer substrate is itself clear. As used in this disclosure, the term "fire retardant" or "flame retardant" is intended to refer to that particular property of a material which provides it with a degree of resistance to ignition and burning. Thus, a fire or flame retardant composition is one which has a low level of flammability and flame spread. This property may be conveniently evaluated by means of any of the standard flame retardancy tests such, for example, as the ASTM test D-635.

In addition to being used as fire retardant additives for the preparation of thermoplastic polymer compositions, the bis(hydrocarbyl) vinylphosphonate copolymers of this invention may be used in any of the various coating, adhesive, laminating, impregnating and molding applications known to those skilled in the art. Thus, they may be coated upon and/or absorbed by all types of substrates to which it is desired to impart fire retardant properties. They may, therefore, be used as coatings, impregnants, fillers, laminants, and adhesives for such substrates as wood; paper; metals; textiles based on either natural or synthetic fibers or blends thereof; synthetic polymer films such as those based upon polyolefins, regenerated cellulose, i.e. cellophane, polyvinyl chloride, polyesters and the like; leather; natural and synthetic rubber; fiberboard; and synthetic plastics prepared by means of either addition or condensation polymerization techniques.

Any desired thermoplastic polymers may be blended with the above described bis(hydrocarbyl) vinylphosphonate copolymers in order to prepare fire retardant compositions. Such thermoplastic polymers include:

1. the homopolymer of methyl methacrylate, i.e. polymethyl methacrylate, as well as copolymers of methyl methacrylate with minor proportions of one or more alpha, beta-ethylenically unsaturated monomers which are polymerizable therewith including: the $C_1$–$C_8$ alkyl, cycloalkyl and bicycloalkyl esters of acrylic acid and the $C_2$–$C_8$ alkyl, cycloalkyl and bicycloalkyl esters of methacrylic acid such, for example, as ethyl acrylate and methacrylate, butyl methacrylate, ethylhexyl methacrylate, norbornyl acrylate, and cyclohexyl acrylate; vinyl aryl compounds such, for example, as alpha-methyl styrene and styrene; and, nitriles of alpha, beta-ethylenically unsaturated carboxylic acids such, for example, as acrylonitrile and methacrylonitrile. From the above given group, the use of the $C_1$–$C_{18}$ alkyl esters of acrylic acid, particularly ethyl acrylate, and of the $C_2$–$C_8$ alkyl esters of methacrylic acid is preferred.

2. acrylonitrile-butadiene-styrene resins, commonly referred to as "ABS" resins which generally comprise either a mixture of a 60 to 80:40 to 20 styrene:acrylonitrile copolymer with from about 10 to 40%, by weight of a 5 to 40:95 to 60 acrylonitrile:butadiene copolymer or a mixture of a 60 to 80:40 to 20 styrene:acrylonitrile copolymer with from about 10 to 40%, by weight, of a graft of the latter copolymer onto polybutadiene.

3. poly(alpha-olefins) such as polypropylene and polyethylene and copolymers of one or more alpha-olefins, such as ethylene or propylene, with a minor proportion of one or more ethylenically unsaturated monomers including 4-methyl pentene-1; butene-1; norbornene and its derivatives; (EPDM) cyclopetadiene; cyclopentene; cyclobutene; vinyl acetate; the $C_1$–$C_{12}$ alkyl acrylate and methacrylate esters; as well as blends of the homo- and copolymers of alpha-olefins with other types of thermoplastic polymers.

4. polystyrene and copolymers of styrene or alphamethyl styrene with a minor proportion of one or more ethylenically unsaturated comonomers such, for example, as nitriles of ethylenically unsaturated carboxylic acids including acrylonitrile and methacrylonitrile; and $C_1$–$C_{12}$ alkyl esters of acrylic and methacrylic acid such, for example, as methyl methacrylate and 2-ethylhexyl acrylate; and graft copolymers of styrene or alpha-methylstyrene with polybutadiene and other hydrocarbon elastomers.

5. cellulosic resins including cellulose esters and mixed esters such, for example, as cellulose nitrate, cellulose acetate, cellulose butyrate, cellulose propionate, cellulose acetate-butyrate, cellulose acetate-propionate and cellulose ethers such, for example, as ethyl cellulose;

6. polyamide resins, i.e. the resins made by the condensation of di- or polyamines with di- or polybasic acids or by polymerization of lactams or amino acids. Typical polyamides include: nylon 4 which is made from pyrrolidone; nylon 6 obtained by polycondensation of caprolactam; nylon 66 obtained by the condensation of hexamethylene diamine with adidic acid; nylon 610 obtained by the condensation of hexamethylenediamine with sebacic acid; nylon 7 which is a polymer of ethyl aminoheptanoate; nylon 9 made from 9-aminononanoic acid; and nylon 11 made from 11-amino undecanoic acid;

7. polyester resins, i.e. the resins produced by the condensation of saturated or unsaturated dibasic acids, such as terephthalic, maleic, fumaric, isophthalic, adipic and azelaic acids with dihydric alcohols such as ethylene glycol, propylene glycol, diethylene glycol and dipropylene glycol. Where the resin is made with an unsaturated acid, a polymerizable monomer such, for example, as styrene, vinyl toluene, diallyl phthalate, methyl methacrylate; chlorostyrene, alpha-methyl styrene, divinyl benzene or triallyl cyanurate is often included in the composition;

8. polyurethane resins, i.e. the resins formed by the reaction between a bi- or polyfunctional hydroxyl containing compound, such as a polyether or polyester, and a di- or polyisocyanate such as toluene diisocyanate or diphenylmethane-4, 4'-diisocyanate;

9. polycarbonate resins, i.e. the resins derived from the reaction between a difunctional alcohol or phenol, such as bisphenol A, and phosgene or an alkyl or aryl carbonate;

10. polyacetal resins, i.e. the resins derived from the anionic polymerization of formaldehyde to obtain a linear molecule of the type $—O—CH_2—O—CH_2—O—CH_2—$;

11. polyphenylene oxide resins made by the oxidative polymerization of 2,6-dimethylphenol in the presence of a copperamine-complex catalyst;

12. polysulfone resins, i.e. the resins containing an $SO_2$ linkage as derived from the reaction of sulfur dioxide with olefins such as 1-butene or, more preferably, by reaction of bisphenol A with 4,4'-dichlorodiphenyl sulfone.

13. the acrylate:styrene:acrylonitrile resins, commonly referred to as "ASA" resins, which comprise a copolymer containing a major proportion of a $C_2$-$C_8$ alkyl acrylate elastomer upon which is grafted about 80–72% of the weight of the latter copolymer of a 70–80:30–20 styrene:acrylonitrile copolymer.

In effect, one may utilize any thermoplastic polymer, i.e. any polymer that may be softened by heat and then regain its original properties on cooling, in preparing the fire retardant compositions of this invention.

The actual blending of the copolymer additives of this invention with the selected polymeric substrate, i.e. with any one or more of the above described thermoplastic polymers, may be accomplished by means of any convenient procedure which will result in an intimate admixture of the additive within the mass of the substrate polymer. Thus, for example, an aqueous suspension containing the particles of the copolymer additive may simply be blended or otherwise admixed with the substrate polymer which should, preferably, be in the form of an aqueous latex or suspension. Or, if desired, the copolymer additive and the thermoplastic polymer substrate may be admixed while each is in the form of a solid powder.

The blending operation may also be carried out by means of a procedure in which the thermoplastic polymer which comprises the substrate is itself polymerized while in the presence of an aqueous emulsion or suspension or organic solvent solution containing one or more of the previously polymerized copolymer additives of this invention. Alternatively, the bis(hydrocarbyl) vinylphosphonate containing copolymer additive may be polymerized in a system which contains the previously polymerized selected thermoplastic polymer substrate in an appropriate physical form, e.g. as an aqueous suspension or emulsion or as an organic solvent solution.

With respect to proportions, the amount of bis(hydrocarbyl) vinylphosphonate containing copolymer which may be admixed with a thermoplastic polymer substrate will depend, primarily, upon such factors as the particular phosphonate copolymer and thermoplastic polymer substrate which are to be blended with one another, the degree of fire retardancy desired in the resulting blend, the degree of clarity, hardness and other specific physical properties which are sought as well as other technical and economic considerations known and understood by those skilled in the art. However, in order to attain a composition which will be self-extinguishing, it is generally desirable to introduce an effective concentration of the bis(alkyl) vinylphosphonate copolymer additive which will be sufficient to provide the resulting blend with at least about 0.5%, by weight, of phosphorus and with at least about 10%, by weight, of halogen, i.e. chlorine and/or bromine, derived from the halogen containing ethylenically unsaturated monomer and also, if possible, from the bis(hydrocarbyl) vinylphosphonate.

The fire retardant, thermoplastic polymer compositions of this invention can be prepared so as to contain various optional additives which may include plasticizers such as the alkyl esters of phthalic, adipic and sebacic acids such, for example, as dioctyl phthalate and ditridecyl phthalate and aryl phosphate esters such, for example, as diphenyl and tricresyl phosphate, etc.; lubricants and mold release agents such as stearic acid or its metal salts, petroleum based waxes, mineral oils, polyethylene waxes, etc.; and heat and light stabilizers such as barium, cadmium, calcium, zinc soaps or phenates, basic lead compounds, organo-tin compounds, such as dialkyl tin mercaptides and dialkyl tin maleates, thiolauric anhydride and n-butyl stannoic acid, epoxidized oils, alkyl diphenyl phosphites, triaryl phosphites, phenyl salicylates, benzophenones and benzotriazoles, etc. For a more complete listing of plasticizers, lubricants, stabilizers and other functional additives, one may consult "Polyvinyl Chloride" by H. A. Sarvetnick published by Van Nostrand Reinhold Co., New York, N.Y., in 1969.

The compositions of this invention may also contain fillers, pigments, dyes, opacifying agents, decorative additives such as reflective metal foils or flakes, and other imbedded solid objects such as fiber glass, textile fibers, paper, and the like, provided that they do not detract from the flame retardancy of these products. In addition, the compositions may contain other flame retardants such as antimony compounds, halogenated alkyl phosphates or phosphonates, alkyl acid phosphates, or small concentrations of phosphoric acid.

The novel fire retardant compositions of this invention, comprising blends of any of the above described thermoplastic polymers with one or more of the novel fire retardant additives of this invention, may be utilized in any of the coating, impregnating and especially in the molding applications known to those skilled in the art wherein it is desired to provide fire retardancy to the resulting end product. For example, these compositions may be used for preparing such diverse items as calendered films, blow molded bottles, extruded flat bed and blown films, extruded and shaped articles such as panels, sheets, rods and tubes, etc. and in carrying out such processes as injection molding, fluidized bed coating, electrostatic powder spraying and rotational coating, etc. More particularly, these compositions which are optically clear such, for example, as those based upon homo- or copolymers of methyl methacrylate or homo- or copolymers of styrene may be utilized for preparing such articles as lenses, aircraft canopies, windows, windshields, lighting fixtures, and advertising displays. Applications wherein optical clarity is not essential include such automotive applications as seat backs, door panels, instrument panels, head rests, arm rests, package shelves, plated hardware, radiator grills, fender extensions and liners, wheel covers and gas tanks. Non-automotive applications include their use as structural and decorative components for both the interiors and exteriors of conventional houses and mobile homes and as structural and decorative elements of business machines and electrical appliances.

The following examples will further illustrate the embodiment of this invention. In these examples, all parts given are by weight unless otherwise noted.

EXAMPLE I

This example illustrates the preparation of a bis (hydrocarbyl) vinylphosphonate copolymer as well as its subsequent use in preparing a fire retardant, thermoplastic polymer composition.

Into a 32 ounce reaction vessel, there is charged 38g of bis(beta-chloroethyl) vinylphosphonate, hereinafter referred to as "bis-beta"; 75g of a 1% aqueous solution of methyl cellulose; 0.8g of a 75% solution of t-butyl peroxypivalate in mineral spirits; and, 375g of deionized water. The reaction vessel is chilled to a temperature of about 20°C. 112g of vinyl chloride monomer is introduced whereupon the reactor is capped and tumbled end-over-end for 12 hours in a 60°C. constant temperature bath.

The resulting aqueous suspension has a resin solids content of 25%, by weight, of a 75:25 vinyl chloride-bis-beta copolymer having an average particle size of about 200 microns and a Relative Viscosity of 1.75 as determined with a 0.1g/deciliter solution of the copolymer in cyclohexanone at 25°C. After filtering and drying, a small portion of the copolymer solids is methanol extracted in a Soxhlet apparatus and essentially no free bis-beta is found to have been removed thereby indicating that there is no unreacted bis-beta present in the copolymer.

A total of 44 parts of the above described vinyl chloride:bis-beta copolymer, which is in the form of a dry, particulate mass, is intimately admixed with 56 parts of an 80:20 methyl methacrylate:ethyl acrylate copolymer and the resulting mixture, which is found to have a phosphorus content of 1.28%, by weight, and a chlorine content of 21.8%, by weight, is thereupon fluxed on two-roll mill operating at a temperature of 165°C. A 0.065 inch thick sheet is then pressed from the fluxed mixture and is found to have excellent color and clarity comparable to that exhibited by a control which comprises a 0.065 inch thick sheet prepared by the identical procedure as described above using, in this instance, an unmodified batch of the same 80:20 methyl methacrylate:ethyl acrylate copolymer.

The fire retardancy of the control sheet and of the sheet prepared from the novel composition of this invention is then evaluated using the procedure of the ASTM D-635 test. In brief, this test involves preparing 5 × ½ × 0.05 inch specimens from the respective sheets. These specimens are then suspended so that their 5 inch dimension is horizontal and their ½ inch dimension is inclined at a 45° angle. One end of the thus suspended specimen is then contacted, for 30 second periods, with a one inch high flame from a ⅜ inch diameter barrel bunsen burner fitted with a 1⅞ inch wide wing top.

As evaluated by means of the latter test procedure, it is found that the sheet containing the vinyl chloride:bis-beta copolymer additive of this invention is completely non-burning whereas the unmodified control burns at a rate of 1.94 inches per minute until it is entirely consumed.

Comparable results are attained by the use, as fire retardant copolymer additives, of similarly prepared bis-beta-copolymers in which the vinyl chloride is replaced, respectively, with alpha- chloroacrylonitrile, alpha-chlorostyrene and methyl alpha-chloroacrylate.

EXAMPLE II

The suspension polymerization procedure described in Example I, hereinabove, is followed in order to prepare the various bis(hydrocarbyl) vinylphosphonate copolymer additives listed below.

| COPOLYMER NO. | COMPOSITION BY WEIGHT |
|---|---|
| 1 | 84:16 vinyl bromide:bis-beta |
| 2 | 30:50:20 vinyl chloride:vinyl bromide:bis-beta |
| 3 | 60:20:20 vinyl chloride:vinyl bromide:bis-beta |
| 4 | 82:18 vinylidene chloride:bis-beta |

Samples of each of the above described copolymer additives are then intimately admixed with various thermoplastic polymer substrates which include:

| THERMOPLASTIC POLYMER SUBSTRATE NO. | DESCRIPTION OF POLYMER SUBSTRATE (BY WEIGHT) |
|---|---|
| 1 | An 80:20 methyl methacrylate:ethyl acrylate copolymer |
| 2 | An ABS resin sold by Monsanto Chemical Co. under the trademark "Lustran 461" |
| 3 | Polymethyl methacrylate |
| 4 | A 75:25 styrene:acrylonitrile copolymer |

The resulting blends are then used for the preparation of 0.065 inch thick sheets by means of the milling procedure set forth in Example I. The fire retardancy of these sheets, as well as of controls which comprise sheets prepared from samples of the various unmodified thermoplastic polymer substrates, is then evaluated by means of the procedure of the ASTM D-635 test. Table 1 hereinbelow, provides a description of the composition of the various sheets while Table 2 describes the results attained in their fire retardancy evaluation.

TABLE NO. I

COMPOSITION OF SHEETS UNDERGOING EVALUATION

| SHEET NO. | COPOLYMER ADDITIVE NO. | % BY WT. COPOLYMER ADDITIVE | THERMOPLASTIC POLYMER SUBSTR. NO. | %, BY WT. THERMOPLASTIC POLYMER SUBSTR. | % BY WT. PHOSPHORUS | % BY WT. HALOGEN |
|---|---|---|---|---|---|---|
| 1 | 1 | 44 | 1 | 66 | 0.94 | 29.6 |
| 2 | 2 | 44 | 1 | 66 | 1.17 | 26.6 |
| 3 | 3 | 50 | 2 | 50 | 1.80 | 27.6 |
| 4 | 3 | 36 | 2 | 64 | 1.40 | 18.2 |
| 5 | 3 | 50 | 3 | 50 | 1.33 | 27.6 |
| 6 | 3 | 50 | 4 | 50 | 1.33 | 27.6 |
| 7 | 4 | 50 | 1 | 50 | 1.20 | 32.6 |
| 1C | — | 0 | 1 | 100 | 0 | 0 |
| 2C | — | 0 | 2 | 100 | 0 | 0 |
| 3C | — | 0 | 3 | 100 | 0 | 0 |
| 4C | — | 0 | 4 | 100 | 0 | 0 |

TABLE NO. 2

Flame Retardancy Evaluation

| Sheet No. | |
|---|---|
| 1 | Completely non-burning |
| 2 | Completely non-burning |
| 3 | Self-extinguishing as defined by ASTM test D-635 |
| 4 | Self-extinguishing as defined by ASTM test D-635 |
| 5 | Completely non-burning |
| 6 | Self-extinguishing as defined by ASTM test D-635 |
| 7 | Completely non-burning |
| 1C | Burns at rate of 1.94 inches/minute until entirely consumed |
| 2C | Burns at rate of 2.2 inches/minute until entirely consumed |
| 3C | Burns at rate of 2.3 inches/minute until entirely consumed |
| 4C | Burns at rate of 2.3 inches/minute until entirely consumed |

The above given data is clearly indicative of the excellent results that are achieved in the flameproofing of thermoplastic polymers with the novel bis(hydrocarbyl) vinylphosphonate copolymer additives of this invention in a direct comparison with unmodified control specimens, i.e. sheets numbers 1C – 4C, of the identical thermoplastic polymers with which these additives are here blended.

Comparable results, with respect to flame retardancy, are achieved using a copolymer containing 80 parts by weight of vinyl chloride and 20 parts, by weight, respectively of each of the following bis(hydrocarbyl) vinylphosphonate monomers:
  bis(beta-chloroethyl) 1-cyanovinylphosphonate,
  bis(beta-chloropropyl) vinylphosphonate,
  bis(beta-chloroethyl) 1-phenylvinylphosphonate,
  di-n-butyl vinylphosphonate and
  diphenyl vinylphosphonate;

These copolymers being blended with the following thermoplastic polymer substrates:
  an acrylate:styrene:acrylonitrile resin
  polypropylene,
  polyethylene,
  polyurethane,
  polycarbonate,
  cellulose acetate,
  nylon 66 and
  polyphenylene oxide.

Variations may be made in proportions, procedures and materials without departing from the scope of this invention as defined by the following claims.

What is claimed is:

1. An aqueous suspension of particles of a suspension copolymer consisting of:
   1. from about 2.5 to 99%, by weight of at least one bis(hydrocarbyl) vinylphosphonate having the structure:

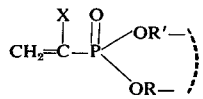

wherein X is selected from the group consisting of hydrogen, halogen, cyano, aryl, $C_1$–$C_{18}$ alkyl and

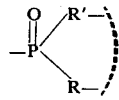

wherein R and R' are hydrocarbyl and substituted hydrocarbyl groups which can be the same, different or conjoint; and
   2. the balance being at least one halogen-containing α, β-ethylenically unsaturated monomer selected from the group consisting of the vinyl halides and the vinylidene halides.

2. The copolymer of claim 1, wherein said vinyl halide is selected from the group consisting of vinyl chloride, vinyl fluoride and vinyl bromide.

3. The copolymer of claim 1, wherein said vinylidene halide is vinylidene chloride.

4. The copolymer of claim 1, wherein said copolymer contains from about 5 to 60, by weight, of said bis(hydrocarbyl) vinylphosphonate.

5. The copolymer of claim 1, wherein said bis(hydrocarbyl) vinylphosphonate is bis(beta-chloroethyl) vinylphosphonate.

6. A dry, particulate mass of the copolymer of claim 1.

7. An aqueous suspension of particles of a suspension copolymer consisting of vinyl chloride and from about 10 to 40, by weight, of bis(beta-chloroethyl) vinylphosphonate.

8. A dry, particulate mass of the copolymer of claim 7.

9. An aqueous suspension of particles of a suspension copolymer consisting of from about 10 to 60%, by weight, of vinyl chloride; from about 10 to 60%, by weight, of vinyl bromide; and, from about 10 to 60%, by weight, of bis(beta-chloroethyl) vinylphosphonate.

10. A dry, particulate mass of the copolymer of claim 9.

11. The copolymer of claim 1, wherein said copolymer has a Relative Viscosity as determined, at 25°C. in a 1% solution of the polymer in cyclohexanone of from about 1.5 to 3.0.

* * * * *

UNITED STATES PATENT AND TRADEMARK OFFICE
CERTIFICATE OF CORRECTION

PATENT NO. : 3,943,085
DATED : March 9, 1976
INVENTOR(S) : Paul Kraft and Siegfried Altscher It is certified that error appears in the above-identified patent and that said Letters Patent are hereby corrected as shown below:

Col. 4, line 49, "o.5" should be -- 1.5 --; and

Col. 8, line 59, "these" should be -- those --;

Signed and Sealed this

Twenty-ninth Day of March 1977

[SEAL]

Attest:

RUTH C. MASON
Attesting Officer

C. MARSHALL DANN
Commissioner of Patents and Trademarks